United States Patent [19]

Wang

[11] Patent Number: 5,260,002
[45] Date of Patent: Nov. 9, 1993

[54] METHOD AND APPARATUS FOR PRODUCING UNIFORM POLYMERIC SPHERES

[75] Inventor: Taylor G. Wang, Nashville, Tenn.

[73] Assignee: Vanderbilt University, Nashville, Tenn.

[21] Appl. No.: 812,647

[22] Filed: Dec. 23, 1991

[51] Int. Cl.$^5$ .................. B01J 13/14; C08J 3/02; C12N 11/04; B29B 9/00
[52] U.S. Cl. .................. 264/4.1; 435/177; 435/178; 264/7; 264/11; 264/13; 264/4.3
[58] Field of Search ............ 264/4.1, 7, 11, 13; 428/402.2; 435/177, 178

[56] References Cited

U.S. PATENT DOCUMENTS

| | | | |
|---|---|---|---|
| 4,279,632 | 7/1981 | Frosch et al. | 264/9 X |
| 4,324,683 | 4/1982 | Lim et al. | 264/4.3 |
| 4,344,787 | 8/1982 | Wang et al. | 264/9 X |
| 4,352,883 | 10/1982 | Lim | 435/178 |
| 4,391,909 | 7/1983 | Lim | 435/178 |
| 4,643,854 | 2/1987 | Kendall, Jr. et al. | 264/13 X |
| 4,673,566 | 6/1987 | Goosen et al. | 435/178 |
| 4,689,293 | 8/1987 | Goosen et al. | 435/178 X |
| 4,806,355 | 2/1989 | Goosen et al. | 435/240.22 X |
| 4,806,357 | 2/1989 | Garretl et al. | 264/5 X |
| 4,956,128 | 9/1990 | Hommel et al. | 435/178 X |
| 4,960,351 | 10/1990 | Kendall, Jr. et al. | 425/6 |

OTHER PUBLICATIONS

H. Gharapetian et al. "Encapsulation of Viable Cells Within Polyacrylate Membranes", *Biotech. and Bioeng.*, vol. 28, pp. 1595–1600 (1986).

Mattheus F. A. Goosen et al. "Optimization of Microencapsulation Parameters: Semipermeable Microcapsules as a Bioartificial Pancreas", *Biotech. and Bioeng.*, vol. 27, pp. 146–150 (1985).

Hiroo Iwata et al. "Evaluation of Microencapsulated Islets in Agarose Gel as Bioartificial Pancreas by Studies of Hormone Secretion in Culture and by Xenotransplantation", *Diabetes* vol. 38, Suppl. 1, pp. 224–225 (Jan. 1989).

Ales Prokop "An integration of cultivation and purification in membrane bioreactors: production of monoclonal antibodies and lymphokines by microencapsulated hybridomas", *Mol. Biother.*, vol. 1., No. 2 (1988).

Patrick Soon-Shiong "Successful Long-Term Exocrine and Endocrine Function of the Autotransplanted Pancreas in Humans", *Pancreas*, vol. 2. No. 3, pp. 357–361 (1987).

Anthony Sun et al. "An Artificial Endocrine Pancreas Containing Cultured Islates of Langerhans", *Artificial Endocrine Pancreas*, vol. 4, No. 4, pp. 275–278 (Nov. 1980).

P. D. Esser et al. "Dynamics of Vertical Annular Liquid Jets," *Journal Of Fluids Engineering*, Mar. 1984, vol. 106, pp. 45–51.

Wilbert M. Fritschy et al. "Effect of Alginate-Polylysine-Alginate Microencapsulation on In Vitro Insulin Release From Rat Pancreatic Islets," *Diabetes*, vol. 40, Jan. 1991, pp. 37–43.

(List continued on next page.)

*Primary Examiner*—Robert L. Stoll
*Assistant Examiner*—John M. Covert
*Attorney, Agent, or Firm*—Tilton, Fallon, Lungmus & Chestnut

[57] ABSTRACT

The present invention relates to a method and apparatus for producing uniform polymeric spheres with controllable permeability. This invention may be useful for encapsulating living cells or tissue or chemicals or medicines in uniform polymeric spheres. In particular, this invention relates to polymeric microspheres made from polycation and polyanion polymer solutions. An apparatus includes airtight housing 1 having top 3 and bottom 25 chambers. Top chamber 3 includes pressure regulator means 5, stationary polyanion reservoir tank 7, polycation reservoir tank 27, and feed line 9 to adjustable tank 11. Tank 11 is associated with oscillator 13, nozzle 14 and capacitance means 19. Nozzle 14 and oscillator 3 cooperate to form polyanion droplets. In the bottom chamber 25 annular nozzle 50 is used to form an annular jet of polycation solution. The droplets and polycation jet are mixed at minimal impact velocities to form uniform polymeric sphere.

11 Claims, 5 Drawing Sheets

OTHER PUBLICATIONS

M. A. Hoffman et al. "Annular Liquid Jet Experiments," *Transactions of the ASME*, vol. 102, Sep. 1980, pp. 344–349.

James M. Kendall "Experiments on annular liquid jet instability and on the formation of liquid shells," *Phys. Fluids*, vol. 29, No. 7, Jul. 1986, pp. 2086–2094.

J. M. Kendall et al. "Metal shell technology based upon hollow jet instability," *J. Vac. Sci. Technol.*, vol. 20, No. 4, Apr. 1982, pp. 1091–1093.

J. M. Kendall et al. "Fluid- and Chemical-Dynamics Relating To Encapsulation Technology," *Drops and Bubbles, American Institute of Physics*, AIP Conference Proceedings 197, pp. 487–495.

Horace Lamb "Hydrodynamics," Table Of Contents, 1930.

C. P. Lee et al. "A theoretical model for the annular jet instability", *Phys. Fluids*, vol. 29, No. 7, Jul. 1986, pp. 2076–2085.

Franklin Lim "Biomedical Applications of Microencapsulation", 1984.

Franklin Lim et al. "Microencapsulation Islets as Bioartificial Endocrine Pancreas," *Science*, vol. 210, Nov. 21, 1980, pp. 908–910.

M. C. Lee et al. "Sensational Spherical Shells," *Aerospace America*, Jan. 1986, pp. 72–76.

Gregory F. Klomp et al. "Macroporous hydrogel membranes for a hybrid artificial pancreas. II. Biocompatibility," *Journal of Biomedical Materials Research*, vol. 17, pp. 865–871, 1983.

G. M. O'Shea et al. "Encapsulation of Rat Islets of Langerhans Prolongs Xenograft Survival in Diabetic Mice;" *Diabetes*, vol. 35, Aug. 1986, pp. 943–946.

John W. Pollard et al. "Culture of Rabbit Embryos and Isolated Blastomeres in Hydrogel Chambers Implanted in the Peritoneal Cavity of Intermediate Mouse Recipients," *Journal of in Vitro Fertilization and Embryo Transfer*, vol. 5, No. 4, 1988, pp. 207–215.

Samuel H. Ronel et al. "Macroporous hydrogel membranes for a hybrid artificial pancreas. I. Synthesis and chamber fabricaiton," *Journal of Biomedical Materials Research*, vol. 17, pp. 855–864, 1983.

Camillo Ricordi et al. "A Method for the Mass Isolation of Islets From the Adult Pig Pancreas," *Diabetes*, vol. 35, Jun. 1986, pp. 649–653.

Camillo Ricordi et al. "Automated Islet Isolation From Human Pancreas," *Diabetes*, vol. 38, Suppl. 1, Jan. 1989, pp. 140–142.

A. M Sun et al. "Microencapsulation of Living Cells—A Long-Term Delivery System," *Journal of Controlled Release*, vol. 2, 1985, pp. 137–141.

Elizabeth G. Posillico "Microencapsulation Technology For Large-Scale Antibody Production," *Bio/Technology*, vol. 4, Feb. 1986, pp. 114–117.

John C. Shen, "Comparative in Vitro and in Vivo Studies of Microencapsulated and Non-encapsulated Adrenocortical Cells," *Agriculture, Animal Culture and Nutrition, Dissertation Abstracts International*, vol. 45, No. 4, Oct. 1984, p. 1072-B.

METHOD AND APPARATUS FOR PRODUCING UNIFORM POLYMERIC SPHERES

BACKGROUND OF THE INVENTION

Field of the Invention

The present invention relates to a method and apparatus for producing uniform polymeric spheres with membrane permeability varying from semipermeable to impermeable. This invention may be used for encapsulating living cells, or tissue, chemicals or medicines, in these spheres.

Description of the Related Art

Spheres have been produced for various medical and biological applications. One of the most important research goals is the transplantation of microspheres which encapsulate islet cells within a semipermeable polymeric membrane to treat diabetes patients. The porosity of the membrane is controlled such that the membrane is permeable to nutrients and to insulin but not the antibody size molecules, i.e,. the membrane acts as an immunoisolation system. This technique for diabetes treatment has been sought as an alternative to insulin injection and to whole-organ pancreas transplants. Studies on rats have shown that the choice of proper materials results in highly biocompatible membranes which maintain appropriate porosity. (A. M. Sun and G. M. O'Shea, Microencapsulation of Living Cells—A Long Term Delivery System, Journal of Controlled Release, 2 (1985), 137-141.) (G. M. O'Shea and A. M. Sun, Encapsulation of Rat Islets of Langerhans Prolongs Xenograft Survival in Diabetic Mice, Diabetes, Vol. 35, No. 8, August 1986, 943-946.) As the methods for islet cell isolation become more efficient more high yield means of encapsulation must be developed, (C. R. Ricordi, E. H. Finke and P. E. Lacy, A Method for the Mass Isolation of Islets From the Adult Pig Pancreas, Diabetes, Vol. 35, June 1986, 649-653.) (C. R. Ricordi, P. E. Lacy and D. W. Scharp, Automated Islet Isolation From Human Pancreas, Diabetes, Vol 38, Suppl. 1, Jan. 1989, 140-142.)

This type of treatment may be a solution for hormone deficient patients including insulin-dependent diabetes patients. Other applications for semipermeable microspheres are being developed for the controlled release of drugs and chemicals.

The common technique for producing polymer membranes is through the ionic interaction between polycation and polyanion polymers. By controlling the concentration or molecular weight of the polymer solutions and the number of membrane layers, the permeability of the resulting membrane can be altered. Currently, the most widely used methods for forming the polymer microspheres may be described as follows: the liquid droplets from one polyanion monomer solution are formed by means of a drop generator; these droplets are then immersed either directly into another polycation polymer solution to produce the polymer spheres (J. M. Kendall, M. Chang and T. G. Wang, Fluid and Chemical Dynamics Relating to Encapsulation Technology, AIP Proceedings 197, Third Int'l Colloquium on Drops and Bubbles, Monterey, Calif. 1988.) or first into some chemical solution to harden the droplets, and the hardened droplets then react with another polycation monomer solution to form the desired membrane (A. M. Sun and G. M. O'Shea, Microencapsulation of Living Cells—A Long Term Delivery System, Journal of Controlled Release, 2 (1985), 137-141.)

The technique developed by Sun for cell encapsulation has been regarded as one of the most successful methods for microencapsulation of human cells. (A. M. Sun and G. M. O'Shea, Microencapsulation of Living Cells—A Long Term Delivery System, Journal of Controlled Release, 2 (1985), 137-141.) (G. M. O'Shea and A. M. Sun, Encapsulation of Rat Islets of Langerhans Prolongs Xenograft Survival in Diabetic Mice, Diabetes, Vol. 35, No. 8, August 1986, 943-946.) The materials used show good biocompatibility with living cells and the process is simple. In general, the cells to be encapsulated are suspended in 1.5% sodium alginate solution (polyanionic). Droplets of this solution are formed by using a syringe pump with a syringe connected to a controlled air jet and are impacted into 1.1% calcium chloride solution to harden. The gel droplets (i.e. calcium alginate) are then immersed into polylysine solution (polycationic) to form the membrane.

Although successful results have been shown, there are some drawbacks with this method. One is the harmful effect of calcium chloride (used to harden the droplets), on the islet cells which results in a lower yield rate. The other is that the impact of the droplets into the calcium chloride deforms the drops and decentralizes the islet cells due to the deceleration, the cells are pushed onto the boundary of the droplet, and usually a bump will form on the hardened droplet. The imperfect surface of the droplet provides the chance for fibroblastic growth to occur at the point of surface discontinuity and induces an inflammatory reaction. Another drawback is the possibility of limited lifetime of this membrane inside of a body due to the fact that the membrane is biodegradable in time. It is obvious that these obstacles must be overcome before mass production can be achieved.

To address the problem of toxic effect of calcium chloride on the islet cells, Kendall, Chang and Wang suggest that the intermediate step of the gel hardening process may be omitted (J. M. Kendall, M. Chang and T. G. Wang, Fluid and Chemical Dynamics Relating to Encapsulation Technology, AIP Proceedings 197, Third Int'l Colloquium on Drops and Bubbles, Monterey, Calif. 1988.) Instead of directing the droplets into the calcium chloride solution, the droplets are introduced into a chitosan solution. A polymer membrane forms when the droplet penetrates the liquid surface. As the chitosan solution is not harmful to the living cells, there will be no damage done to the encapsulant. However, further investigation reveals that new difficulties arise when the proposed method is applied. First of all, the properties of the calcium chloride solution are totally different from that of the chitosan solution. A 0.2% chitosan solution is about ten times as viscous as the water-like calcium chloride solution and the surface tension may also be changed. The experiments show that it is difficult for the submillimeter-size droplets to penetrate the liquid surface without excess deformation. Higher velocity is required and the penetration time is increased. The high impact velocity results in highly distorted microspheres, while the increased penetration time results in the collision of the second droplet on the penetrating one and the droplets stick together.

As such, a need exists in the industry to provide an apparatus and method to produce uniformly concentric semipermeable microspheres that can encapsulate living cells or tissue. More particularly a need exists in the industry to provide a method to encapsulate living cells and tissue wherein the tissue is encapsulated in a first monomer prior to polymerization so that a broader range of polymers may be used.

SUMMARY OF THE INVENTION

The present invention provides a method and apparatus for producing uniform spheres These spheres may be microspheres (about 200 microns to about 500 microns) or larger spheres (about 500 microns to a few millimeters in diameter), these spheres may be formed from polymeric solutions, and the resulting spheres may be semipermeable or impermeable to bodily constituents such as immunoglobulins.

More particularly, the present invention provides a method for producing uniform polymeric spheres from polyanion and the polycation monomers In particular, this method involves providing droplets of a polyanion monomer solution; providing a stream of polycation monomer solution; and mixing the droplets of a polyanion solution and the stream of polycation solution at minimal impact velocities under polymerization conditions to form uniform polymeric spheres.

This invention also provides a method for encapsulating living cells or tissue in uniform polymeric spheres. This method involves: selecting polycation and polyanion monomers to form a membrane of the desired porosity; admixing a polyanion monomer solution and biological material; generating droplets consisting of the polyanion monomer solution and the biological material falling at a certain vertical velocity; providing a stream of polycation monomer solution wherein the stream of polycation solution forms an annular jet; at approximately the same vertical velocity as the polyanion solution; adusting the radial collapsing velocity of the polycation jet to minimize impact velocities and mixing the droplets and polycation jet under polymerization conditions for a set period of time to form uniform spheres of the desired porosity.

This invention also provides uniform polymeric semipermeable microspheres containing biological material in substantially the center of the microsphere. The microspheres are between about 200 to 500 microns in diameter. The biological material includes living cells such as islets of Langerhans. These microspheres are not permeable to substances with a molecular weight greater than about 150,000 Daltons.

This invention also provides an apparatus for producing uniform polymeric spheres. The apparatus includes an air-tight chamber housing; a first chamber containing a reservoir for a biocompatible polyanion solution; a nozzle to produce a jet of polyanion solution; an oscillator to produce droplets; means for deflecting a certain number of droplets to obtain an optimum ratio of polyanion droplets to polycation (e.g. 2 to 1, 3 to 1, 1 to 1) to produce uniform spheres; a reservoir for a polycation solution; and means to increase pressure in said first chamber; a second chamber containing a nozzle to produce an annular jet of polycation solution at approximately the same vertical velocity as said polyanion droplets; means to mix said polyanion droplets and polycation solution at minimal impact velocities; an oscillator to produce droplets; a tapered tube of sufficient length to allow droplets to polymerize prior to contacting wash solution; and means to wash said polymerized spheres.

BRIEF DESCRIPTION OF THE DRAWINGS

FIGS. 3 A and B shows the effect of pressure on the annular jet flow.

DETAILED DESCRIPTION OF THE INVENTION

Figure 1:
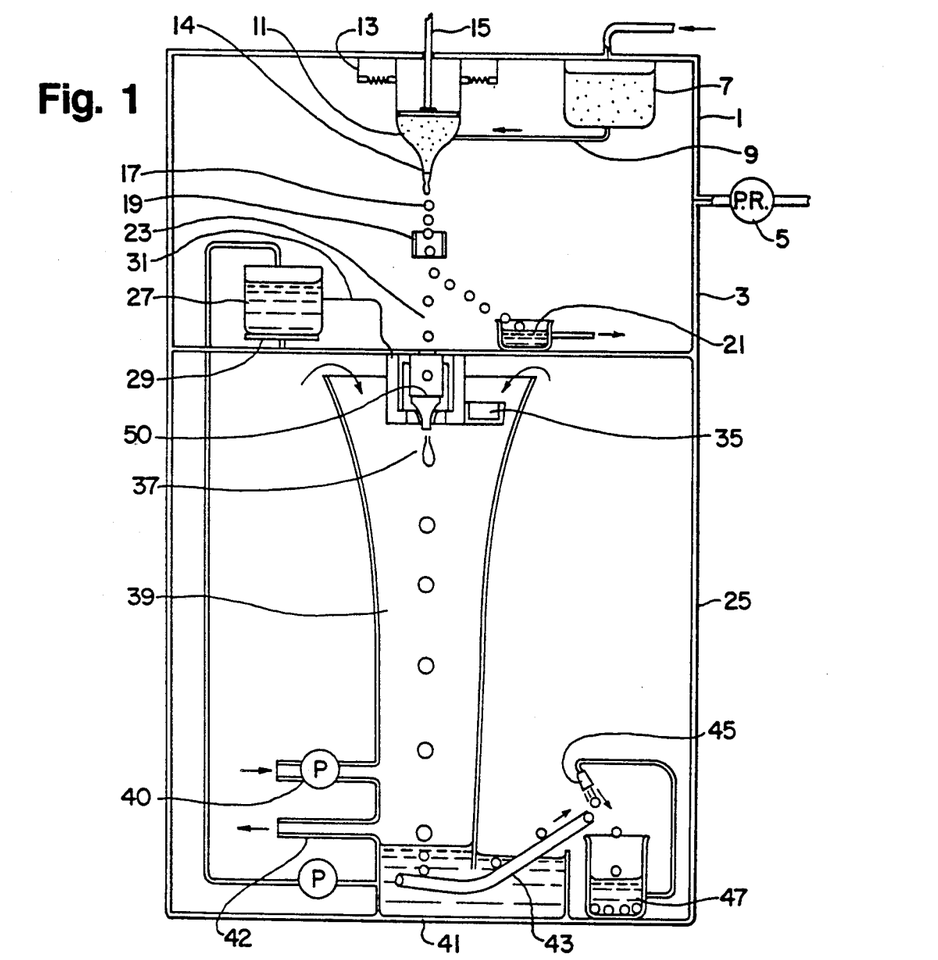
FIG. 1 shows a schematic side view of the apparatus for producing uniform spheres.

Now referring to FIG. 1 a two-chamber-air-tight housing 1 is provided. Top chamber 3 includes an air pressure regulator 5 to increase pressure in the top chamber. Top chamber 3 also includes stationary polyanion solution reservoir 7 and feed line 9 to adjustable tank 11. Tank 11 is associated with oscillator 13 and nozzle 14. Nozzle 14 is used to produce a jet of polyanion solution. The oscillator 13 is used to disperse the jet of polyanion liquid into droplets. The oscillator is tuned to a specific frequency for the solution in Tank 11 to produce a narrow distribution of drops. A liquid column is unstable and will spontaneously break up into droplets due to the disturbance from either the jet itself or external excitation. In general, a wide distribution of drop sizes usually appears when a liquid jet disrupts. This tendency can be suppressed by perturbation of the jet at a single frequency near the most unstable frequency of the jet. The height of the tank 11 can be adjusted to change the hydrostatic pressure of the solution in the tank and thus, the flow rate of the drops.

Tank 11 has a 3 axis traverse 15 to adjust the stream of droplets 17. Capacitance plates 19 are used to deflect polyanion droplets 17 to a storage tank 21 to adjust the flow rate of droplet 23 into the bottom chamber 25 of the two chamber housing. The flow rate of polyanion droplets is adjusted to obtain an optimum ratio of polyanion to polycation droplets. This ratio is experimentally determined based on the polycation and polyanion solution used to form the sphere. For example, a more uniform sphere may be obtained by a flow rate of 2 to 1 polyanion to polycation droplets. If the ratio is not experimentally adjusted the sphere may not have a uniform coating of polymer.

Top chamber 3 also includes a second reservoir 27 containing polycation solution. This reservoir rests on adjustable plate 29. The height of the adjustable plate 29 allows for controlling the flow through rate of the polycation solution.

The droplet diameter produced by this method will be about 1.8 times that of the nozzle diameter. By varying the nozzle diameter, jet velocity, excitation frequency and amplitude, the droplet size as well as the drop formation may be controlled. The rate of formation is the same as the frequency of the excitation, typically betweem 1–4 kHz. The nozzle diameter found to be useful in producing microspheres was in the range from 100 to 700 microns. The vertical jet velocity found to be useful was in the range from 0.5 m/sec to 5 m/sec. The excitation frequency found to be useful was in the range from 1 to 4 kHz, while a minimal amplitude displacement of about 10 microns was observed. The droplets' size was found to vary from about 200 microns to 2 milimeters, although droplets' size directly relates to the monomers and biological material selected, and length of polymerization.

Figure 2:
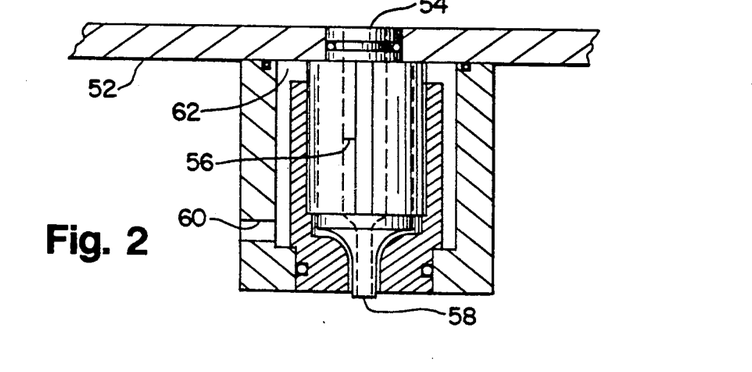
FIG. 2 shows an exploded view of the nozzle for producing the annular jet.
Figure 3A:
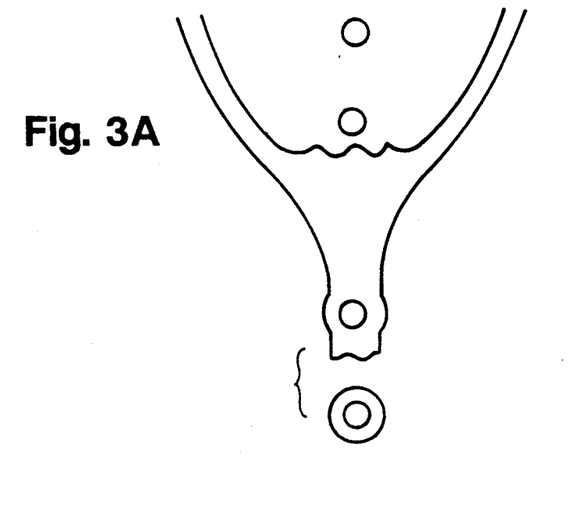
Figure 3B:
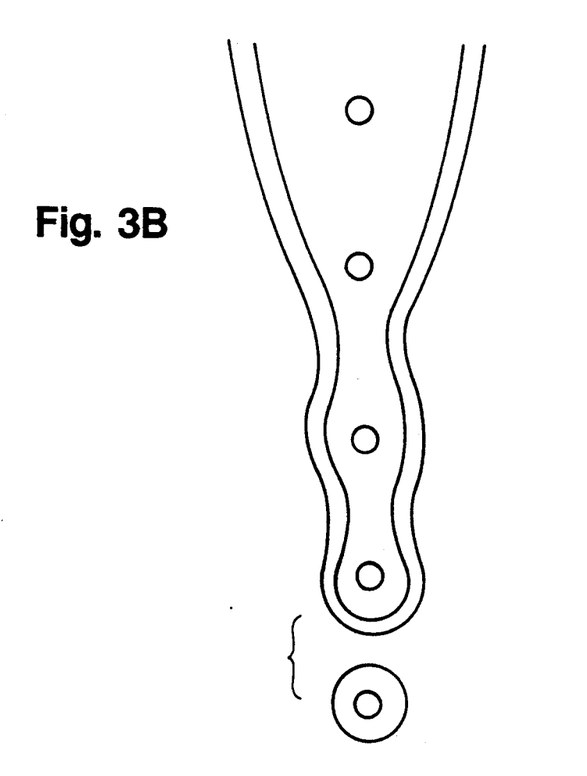

A feed line 31 from reservoir 27 feeds polycation solution from reservoir 27 to nozzle 33. Nozzle 50 provides for an annular jet of polycation solution. Now referring to FIG. 2 a nozzle to produce an annular jet is generally shown by 50. The nozzle is comprised of top plate 52 which is the dividing plane between top chamber 3 and bottom chamber 25. Opening 54 allows droplets 23 to enter the nozzle 50. Funnel 56 conveys droplets to nozzle tip 58. Solution from reservoir 27 enters nozzle 50 at opening 60 and is conveyed to tip 58 by annular space 62. The two solutions flowing at approximately the same relative velocities mix at substantially tip 58. When liquid emerges vertically downward from an annular jet, a conical liquid sheet is formed due to the effects of surface tension, inertia and gravity, and the pressure differential between the inside and the outside of the sheet. Theoretical as well as experimental studies of the annular liquid jet may be found in references (C. P. Lee and T. G. Wang, Dynamics of Thin Liquid Sheet, AIP Proceedings 197, Third Int'l Colloquium on Drops and Bubbles, Monterey, Calif. 1988.) (P. D. Esser and S. I. Abdel-Khalik, Dynamics of Vertical Annular Liquid Jets, ASME J. Fluids Eng., Vol. 106, 1984, pp 45–51.) (M. A. Hoffman, R. K. Takahashi and R. D. Monson, Annular Liquid Jet Experiments, ASME J. Fluids Eng., Vol. 102, 1980, pp 344–349.) (J. M. Kendall, Experiments on Annular Liquid Jet Instability and on The Formation of Liquid Shells, Phys. Fluids, Vol. 29 1986, pp 2086–2094.) The differential pressure between top and bottom 3 & 25 chambers causes the annular jet to collapse at a preset point different than where it would have collapsed if the pressure was equal between top and bottom housing. The concept can be more clearly understood by referring to FIG. 3. In FIG. 3A the pressure between both chambers is equal. Consequently, the jet collapses causing turbulence. The polyanion droplet then enters the polycation stream at more than minimal impact velocities. These impact velocities deform the sphere and do not lead to uniform spheres. While in FIG. 3B the pressure in the top chamber is increased over the bottom chamber to increase the pressure within the annular jet. The point of collapse controlled by the radial collapsing velocity of the jet, is delayed until the jet envelopes the droplet. Then the solution and drops are combined at minimal impact velocities. The collapse occurs radially to form a spherical product.

Additionally, in an alternative embodiment a surfactant such as TRITON can be added to the mixture to reduce the surface tension of the annular jet. The point of collapse can also be delayed in this manner to reduce or eliminate the impact velocities of the droplet and solution.

The alternative method proposed here for producing spheres is that, instead of submerging the droplets into a stationary liquid surface, the stream of droplets is directed into a collapsing annular liquid sheet. By matching the speed of the liquid sheet to that of the droplets, and controlling the collasping velocity of the liquid sheet on to that of the drops impact may be minimized.

An oscillator 35 caused the polymer to disperse as a droplet 37. In a tapered tube 39 the falling droplet 37 polymerizes to form a microsphere. The tube 39 is used to allow droplets to completely polymerize prior to contacting the wash solution. Additionally, the tube is used to provide spheres wherein the biological material is in substantially the center of the sphere. It has been observed by the inventor that when an encapsulating solution has low viscosity the biological material may sink to the bottom or rise to the top of the sphere. If this occurs the microsphere may contain a bump or protrusion and not be uniformly concentric. The inventor has discovered that if air is withdrawn at tube 40 at the rate of acceleration of the sphere, then no gravitational forces will act on the sphere. The required air velocity depends on the configuration of the tube and the viscosity of the polymerization solution and the density of the encapsulated material.

In the present embodiment a tapered tube 39 is used to reduce gravitational effects so that any contents of microsphere do not settle to the bottom or rise to the top of the microsphere while falling, Kendall et al., U.S. Pat. No. 4,960,351. The tapered tube 39 has an air intake 44 that is two feet by 8 inches wide. The tube 39 is 10 feet long and tapers to square 7.22 inches wide on a side. A tube 42 to a servo-controlled exhaust fan draws air through the tapered tube 39. It should be noted that the tube may be straight or tapered. Additionally, in an alternative embodiment where the polymerization solution has a high viscosity air is pumped into the bottom of the tapered tube 39 at pump 40 to slow the fall of the sphere and rotate the sphere to prevent settling of any contents to one side of the microsphere.

The porosity of the membrane can be experimentally controlled from impermeable to semi-permeable. The factors affecting porosity are 1) selection of the monomers 2) length of polymerization time 3) and, monomer molecular weight.

Gelatin is the most common polycation used for film complexation since is coacervates with many polyanions. Alginate, polyphosphate, carageenan and mixed ethylene-maleic acid copolymers have traditionally been employed for the polyanion. Crosslinking can be enhanced by the addition of small molecules such as aldehydes. The selection of the polyelectrolytes used is critical in terms of biocompatibility and nondegradability. It is also important in the control of molecular weight since different naturally occurring polymers will have a fixed molecular weight. The polyanion and polycation selection will also influence the complex reaction time and thereby the pore size. This will facilitate the control of the membrane properties by choosing alternate systems should it not be possible to synthesize less porous structures by varying the contact time between two polyions or molecular weight.

Polyelectrolyte complexes form through the reaction of a polycation and a polyanion. The resulting complex can either remain in solution, precipitate as a gel or separate into two phases: dilute and a concentrated complex coacervate phase. Indeed a complex coacervate is simply defined as a liquid phase containing a high concentration of two oppositely charged polyions. The primary forces of attraction are electrostatic, however, hydrogen bonding, ion-dipole and hydrophobic interactions can also contribute. The most suitable complexes have been formed by the reaction of polyacids and polybases with pK values below two. Since the ionic content of the polyelectrolyte is strongly dependent of the pH of the solution the microstructure of the resulting membrane is also highly pH sensitive. Salts, due to their ion-shielding ability, also have a large influence on the membrane formation kinetics and the final properties. Another important parameter is the ratio of cationic to anionic polymer. For virtually any polymer chemistry the maximum in the water swelling ability (related to permeability) is achieved at a ration 1:1. The complex formation can be strengthened (tighter network) by increasing the charge density along the polymeric backbone. This variable can be particularly well adjusted if a synthetic polyelectrolyte is employed. Various investigators have concluded that the stability of the complex increases with the chain length, or molecular weight of the polyelectrolyte. Typical polymers have chain lengths in the 500-3000 range. The thin film polysalt complexes have been reported to form either "spontaneously" or in a "rapid and complete reaction". This rapid formation occurs as long as the polyanion and polycation exceed a critical concentration of approximately 0.6% wt %. Because of the impermeability of this film to large molecules such as the two polyions the reaction stops after the initial formation of the membrane. In terms of the network microstructure the ionic crosslinks are random with properties similar to other hydrogels. Kamide has indicted that the polymer concentration has little effect on the pore structure or size for phase inversion membranes (K. Kamide and S. -I. Manabe, "Materials Science of Synthetic Membranes," American Chemical Society, Washington, D.C. 1985). However, others have found very small polymer concentration dependencies for polymers made from cellulose or polyamides (increasing the polymer concentration decreased the pore size and porosity).

The binding between the polyanion and polycation is nearly athermal, with a typical heat of reaction of 1.9 kcal/mol. The driving force for the complex formation is entropic and is governed by the release of microions from the network domain to the bulk solution. Several techniques have been employed in the investigation of complex formation including nephelometry, conductance, potentiometry, electrophoresis, pH measurements, calorimitry, and metahromatic dyes.

The polymerized sphere enters bath 41 with filter cloth 43. Finally, the spheres are washed 45 and deposited in a storage buffer 47.

Suitable polymers for the formations of polyelectrolyte complexes would include three categories of materials: 1) those materials with prior NIH approval for human implantation (Table 1), 2) natural polymers (Table 2), and 3) synthetic materials (Table 3). We will also consider membranes produced from the condensation of nonionic homopolymer films, or the formation of complexes between polymers and a second component which is a complexing simple electolyte.

TABLE 1

| Materials with NIH Approval for Implantation | |
|---|---|
| 1) Polyacids: | Polyacrylates (e.g. sodium) |
| | Polymethacrylates |
| | Olefin-Maleic anhydride copolymers |
| 2) Polyesters: | Poly glycolic acid |
| | Poly lactic acid |
| | Poly caprolactane |
| | copolymers of the above species |
| 3) Polyorthoesters: | Polydioxyalkyltetrahydrofuran |

TABLE 1-continued

| Materials with NIH Approval for Implantation | |
|---|---|
| 4) Hydrogels: | Poly 3,9-bismethylene-2, 4,8,10 tetra aspiro 5,5 undecane-co-1,6 hexanediol |
| | Hydroxyethylmethacrylate |
| | Polyethyleneglycol monomethyacrylate |
| | Gelatin crosslinked with formaldehyde |
| 5) Polysaccharides: | Cellulose |
| | Dextran |
| 6) Polypeptides: | Poly glutamic acid |
| | Glutamic acid leucine copolymers |
| | Polyaminotriazole |
| | alkyleneaminotriazole copolymers |
| | Albumin beads (Albumin crosslinked with glutaraldehyde |
| 7) Amino Acid Polymers | Poly D- or L-lysine HCL |
| | Poly D- or L-ornithine HCL |
| | Poly D- or L-arginine |

TABLE 2

Naturally occurring Water Soluble Polymers and Polyelectrolytes

Polysaccharides (−): starch, gums, carrageenans, dextran, xanthan
Sulfated algal Polysaccharide (−)
Alginate (−)
Hyaluronic acid films (−)
Heparin (−)
Chondroitin sulfates (−)
Polygalacturonic acid (−)
Alginic acid (−)
Sodium carboxymethylcellulose (−)
Sodium carboxymethylcellulose-diethylaminoethyldextran copolymer[1] (−)
Agar
Hyaluronate (−)
Sulfated hyaluronic acid (−)
Sulfated deacetylated hyaluronic acid (−)
Heparin (−)
Polyguluronate (normal or acetylated) (−)
Polymannuronate (−)
Chondroitin sulphate (−)
Ascopyllan (−)
Pectin (made of 1,4 polyglacteronic acid) (−)
Dextran sulfate (−)
Fucoidan (−)
Oxdized cellulose (−)
Polypeptides and Proteins (4 types): 1) hydrophobic e.g. polyphenylalanine 2) polar e.g. serine 3) acidic (−) e.g. asparatic acid, chondroitin-6-sulfate, heparin, human serum albumin 4) basic (+) e.g. lysine, l-argine, collagen
Polyneucleic acids (RNA,DNA) (nonionic)
Pullan (nonionic)
Cellulose (nonionic)
Algal Pectin
Modified Celuloses: Hydroxypropylcellulose (nonionic, forms a thin film), Hydroxypropylcellulose (nonionic),
Carboxymethylcellulose (nonionic); forms a gel/film
Diethylaminohydroxypropylcellulose (+),
Diethylaminoethylcellulose (+)
Chitosan (+)[2]

[1]By varying the pH you can adjust the copolymer composition in the membrane. pH, therefore, may be an important tool in the complex formation.
[2]Chitosan is composed of 2-amino-2-deoxy-D-glucose (D-glucosamine) and 2-acetamido-2-deoxy-D-glucose (N-acetyl-D-glucosamine) which are both common substituents in the human body. It is commercially available from crab or shrimp shells, to form chitin, which is then converted to Chitosan-ammonium salt. It is therefore a logical starting point for the polycomplex membrane formation.

TABLE 3

| Synthetic Polymers for film of Polyelectrolyte complex formation | |
|---|---|
| Nonionic. | Polyacrylamide |

TABLE 3-continued

Synthetic Polymers for film of
Polyelectrolyte complex formation

| | |
|---|---|
| | Polymethacrylamide |
| | Polyvinyl alcohol films. |
| Anionic. | Poly sodium acrylate |
| | polystyrene sodium sulphate |
| | Polyvinyl sulphonic acid salts |
| | Polyvinyl benzoic acid salts |
| | Polyvinyloxypropanesulphonic acid salts |
| | Poly 4-vinylphenol salts |
| | Polyvinylsucciniumidum acid salts |
| | Sodium-2-sulfoxyethyl methacrylate |
| | Sodium-2-acrylamido-2-methylpropane sulphate |
| | Sodium-3-acrylamido-3-methyl butanoate |
| Cationics. | Dimethylaminoethyl methacrylate |
| | Dimethylaminoethyl acrylate |
| | Diethylaminoethyl methacrylate |
| | Diallydimethylammonium chloride |
| | Metharylryloxyethyltrimethyl ammonium sulfate |
| | Metharylryloxyethyltrimethyl ammoniumchloride |
| | 3-methacrylamidepropyltrimethyl ammonium chloride |
| | Polyvinyl pyridine (Blood plasma substitude) |
| | Quaternerized polyvinylpyridine |
| | Polyethyleneimin, linear |
| | Polymethylene-N,N-dimethyl piperdinium |
| | Polyvinyl 4-alkyl pyridinium |
| | Polyvinylbenzenetrimethyl ammonium chloride |
| | 2-acrylamido-2-methylpropanedimethylammonium chloride |
| | 1,3 sulfopropyl-2-vinyl pyridinium |

The present invention may be used for encapsulating living cells, or tissue, chemicals or medicine, in uniform spheres The material so encapsulated is referred to as an encapsulant. The encapsulant may be liquid or solid. For example, if a nonpermeable sphere or microsphere is formed a drug can be encapsulated in the sphere or microsphere for either timed release or chemical release of the drug in the body. In the situation of timed release of the drug, the thickness of the sphere or microsphere wall can be adjusted, for example by increasing the number of membrane layers to facilitate timed delivery of the drug. Additionally, certain organs or tissues can be targeted for specific release of the drug. The sphere or microsphere wall can degrade in the presence of certain chemicals or heat. One good example of this use would be in localized chemotherapy.

EXAMPLE 1

Fresh solution of polyanion, e.g. 1.4% sodium alginate and polycation solution, e.g. 0.2% chitosan solution were prepared. The viscosity of the polyanion solution was determined to be 54 cp. Plastic beads with density of 1.04 and sizes between 100 and 150 microns were used to simulate the encapsulation process of islets cells which has a density of about 1.05 and size of about 150 $\mu$m. The beads were admixed with the polyanion solution. The polyanion-beads solution was transferred to the first reservoir. Air pressure was supplied to the reservoir to force the liquid flow to the first nozzle through a tube. The barrel diameter of the nozzle was 200 microns. The air pressure was adjusted to obtain a hydrostatic pressure needed to have laminar flow of the polyanion jet. The oscillator connected to the first nozzle was then turned on. The frequency and amplitude of the oscillator were adjusted so that the polyanion jet broke up into uniform size droplets. In this particular experiment the frequency of the oscillator was adjusted to between 1-4 KHz. The droplet size selected was between 300 to 400 microns. The microspheres were observed to determine if each sphere contained a bead. If not, the concentration of beads in the sodium alginate solution of reservoir one was increased. At this time the polyanion jet is turned off.

The polycation solution, 0.2% chitosan, was transferred to reservoir two. Air pressure was supplied to the reservoir to force the liquid flow to the annular nozzle through a tube. The air pressure was adjusted to obtain a hydrostatic pressure needed to have laminar flow of the polycation annular jet. The polyanion jet along with the oscillator were turned on. The direction of the droplet stream was adjusted such that the stream was falling in the annular jet. The air pressures in the two reservoirs were adjusted such that the vertical speed of the droplet and collapsing annular jet matching each other.

Deformation of the spheres was avoided by minimizing the impact velocities. The droplet was submerged into the liquid sheet at approximately the same relative vertical velocity, i.e. they were falling almost at the same rate. In this example the velocity of the droplet and the annular jet was about 2.2 m/sec and the polyanion droplet was placed slightly off the center of the polycation stream to avoid turbulence.

Figure 8:
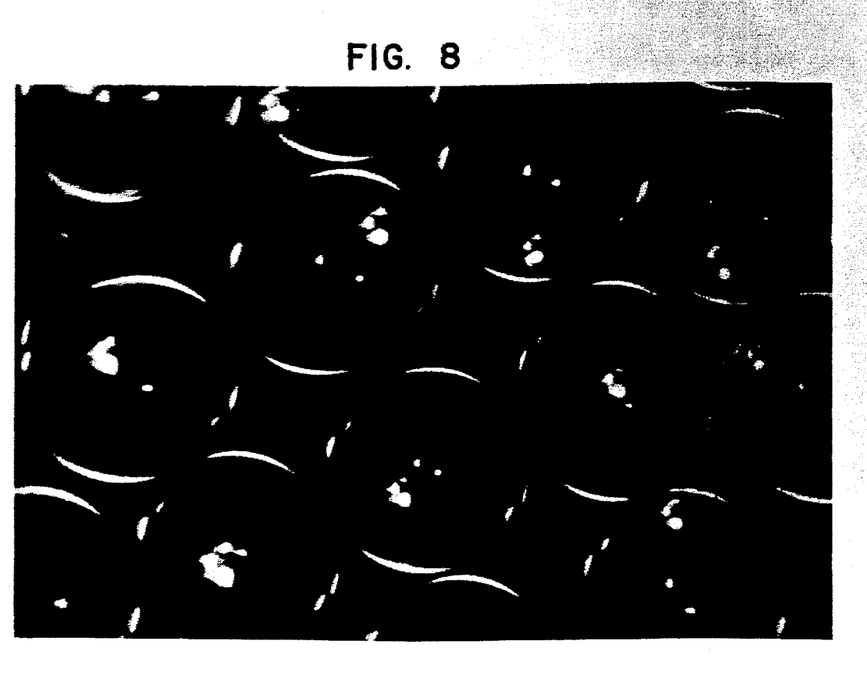
FIG. 8 is a photograph of spheres encapsulating a bead made by the present method.
Figure 9:
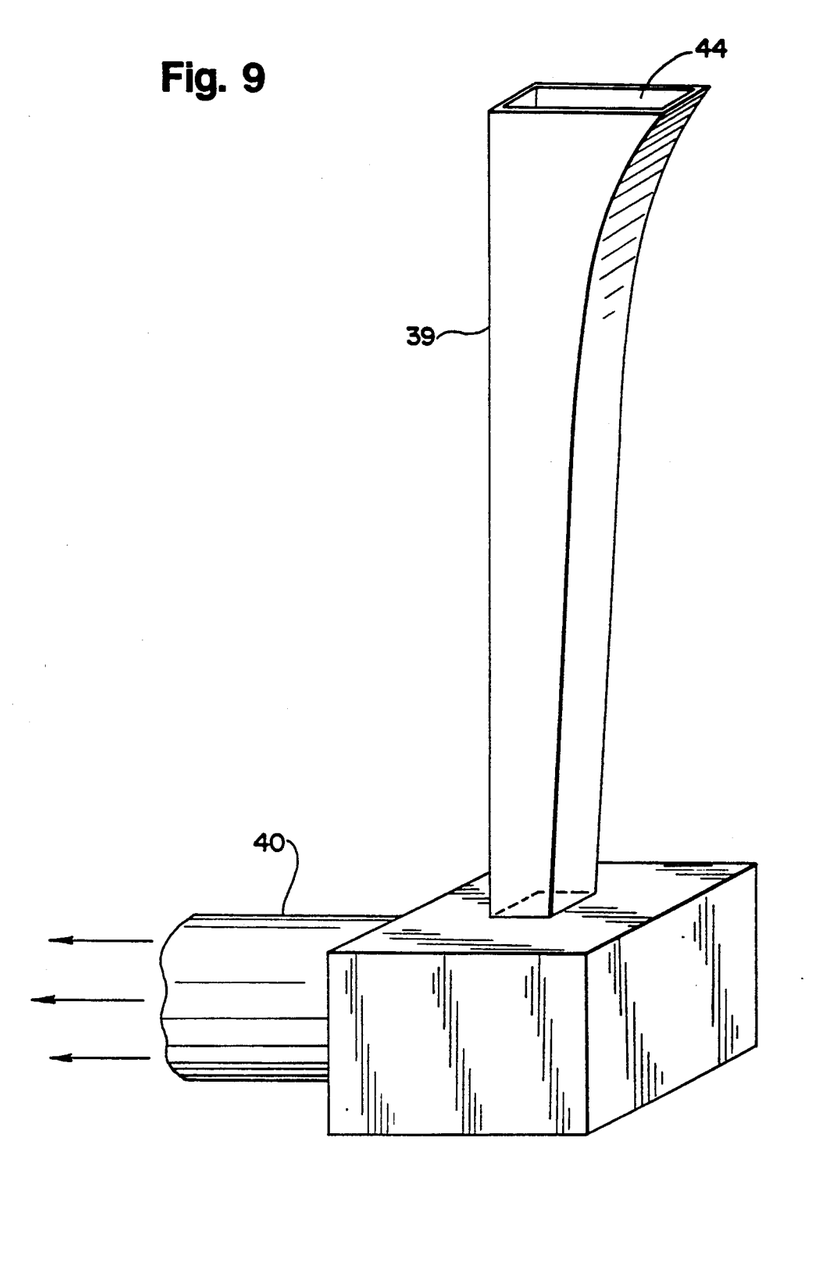
FIG. 9 shows a schematic view of a tapered tube.

This example shows using an annular jet to minimize the impact deformation by matching the vertical velocities of droplet and annular jet. In this case, there was no attempt to minimize the radial velocity of the annular jet caused by the collapsing of the liquid sheet. Photograph of uniformly concentric microspheres with encapsulated plastic beads are shown in FIG. 8. The size of the spheres is about 700 $\mu$m.

EXAMPLE 2

This example illustrates the effect of impact on the deformation of a sodium alginate droplet entering a stationary calcium chloride solution. For the purpose of photography, larger sodium alginate droplets, i.e, size of 2.8 mm, were used. In order to have similar fluid dynamic responses, the Weber number, which is a ratio of kinetic energy and surface energy, was used to ensure that the larger droplet would have about the same impact response as the smaller one.

According to the measurement done by Kendall, Change and Wang (J. M. Kendall, M. Change, T. G. Wang, Fluid and Chemical Dynamics Relating to Encapsulation Technology, AIP Proceedings 197, Third Int'l Colloquium on Drops and Bubbles, Monterey, Calif. 1988), the surface tension of the alginate solution is close to that of water. In general, the droplets used for producing microspheres are in the range of 350 $\mu$m to 450 $\mu$m with an impact speed between 2 m/sec and 4 m/sec. Because of the size differece, the impact speed of the 2.8 mm droplets was reduced to 1 m/sec to keep the ratio of the Weber number between the small droplets and the larger ones in the range of 0.5 to 2.

Figure 4:
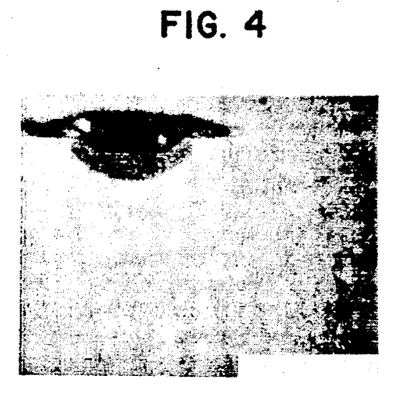
FIG. 4 is a photograph of a sphere having impact deformation.
Figure 6:
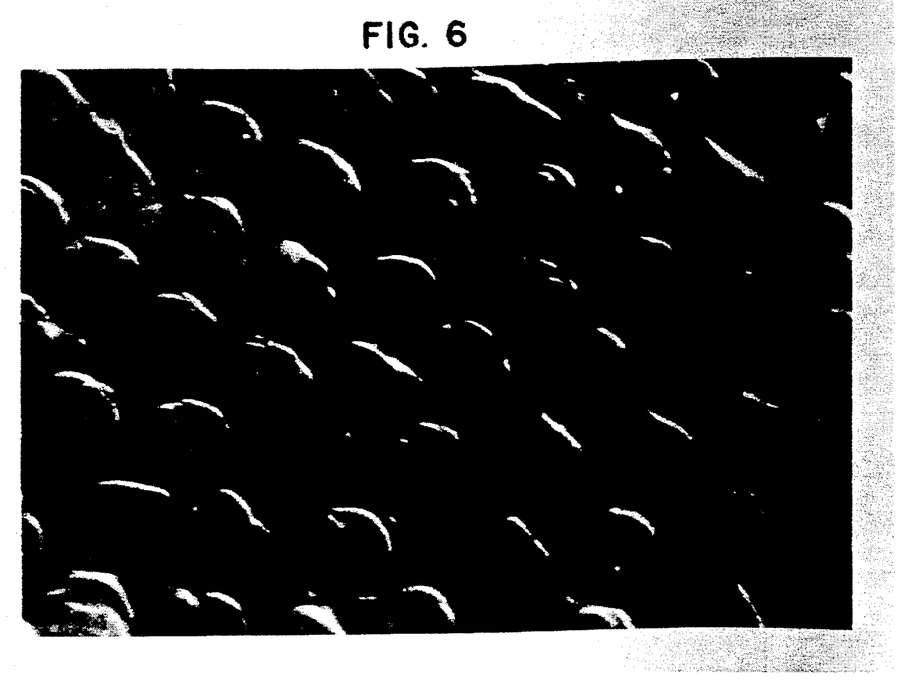
FIG. 6 is a photograph of spheres having impact deformation.

The droplets were made of 1.4% sodium alginate and 0.8% NaCl solution with a viscosity of about 54 cp. FIG. 4 shows the deformation of the droplet when entering the $CaCl_2$ solution. The impact reduces the velocity of the droplet to almost zero within a couple of milliseconds and the dimension of the droplet in the direction of impact is flattened to less that half of the droplet diameter. If the droplet contains a seed, the deceleration due to the impact will push the seed on to the boundary of the droplet, hence a small bump on the outer surface will be produced. This nonperfect surface is then "frozen" by the chemical reaction of sodium alginate and $CaCl_2$ solution. See FIG. 6.

In addition to the nonsmooth surface, there are two facts which may affect the survival of the encapsulant. First, the extremely high deceleration may cause irreversible damage to the encapsulant. Second, after the impact the seed is very close to the boundary and is immobilized by the effect of high liquid viscosity and subsequently the gelling process. As the $CaCl_2$ is toxic to the living cells, the closer the cells are to the boundary, the higher the chances for the cells to be damaged by the $CaCl_2$ solution.

EXAMPLE 3

Figure 5:
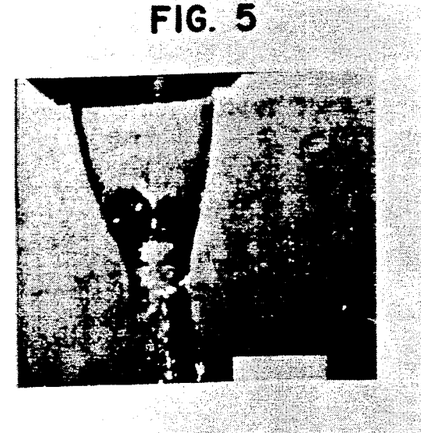
FIG. 5 is a photograph of a sphere made by matching vertical velocities of the droplet and annular jet.

This example illustrates the impact process when the annular jet was used. The impact response was studied by using an annular nozzle of 1 cm size with the thickness of the liquid sheet about 0.3 mm. The speed of the liquid sheet at the nozzle exit was measured by volume rate, which was controlled by feeding reservoir. The speed of the 2.8 mm single alginate droplet, which was generated through a fine syringe needle, was adjusted by changing the location of the syringe needle tip to match that of the $CaCl_2$ liquid sheet at the annular jet exit. The resulting photo FIG. 5 shows the droplet entering the annular jet. The speed used in this study was about 1.5 m/sec for both the droplet and the annular jet. The droplet was kept slightly off center to avoid the turbulence at the center of the collapsing sheet. There is little distortion when the droplet is submerged into the liquid sheet and the spherical shape was maintained through the whole process. In this example, no pressure difference was applied between the annular sheet and outside pressure to minimize the radial velocity component of the liquid sheet. This example shows that the using of an annular jet does indeed eliminate the deformation due to impact, even when the radial is not minimized.

EXAMPLE 4

Figure 7:
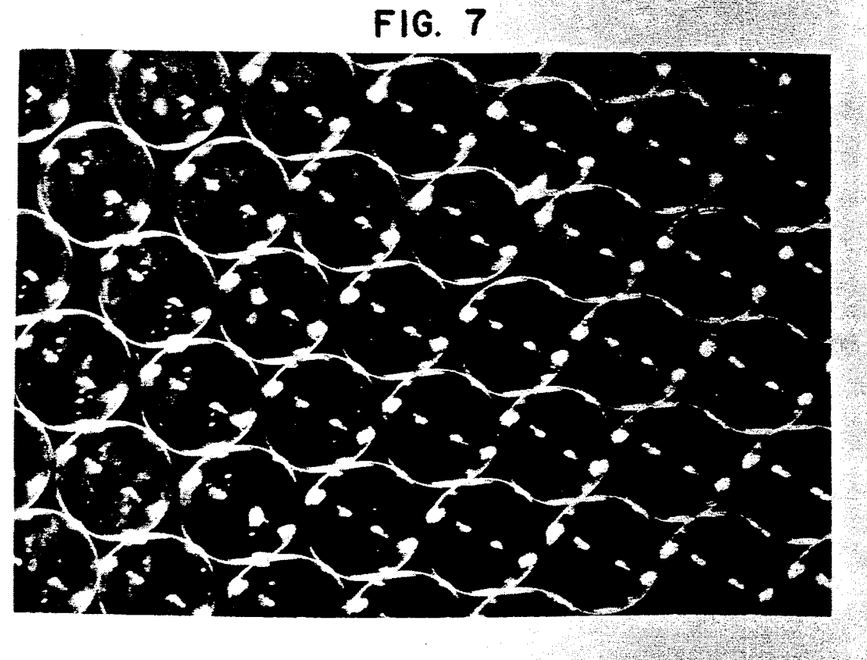
FIG. 7 is a photograph of spheres made by the present method.

This example illustrates the applicability of this invention to produce microspheres directly from polyanion and polycation polymers. The tested materials were chosen as alginate droplets and chitosan solution. The size of the droplet was about 400 $\mu$m. The size of the annular jet is about 4.5 mm with the thickness of the liquid sheet about 0.15 mm. The free fall time of the droplet in the chitosan liquid column is kept such that the chemical reaction is completed before the liquid is collected into a beaker. Note that the reaction between the alginate droplet and the chitosan solution only takes place on the surface of the droplet. The spheres are about 700 $\mu$m. The forming of a membrane on the surface of the alginate droplet increases the drop size from 400 $\mu$m to 700 $\mu$m. See FIG. 7.

In this particular example, a semipermeable sphere not permeable to substances with a molecular weight greater than about 150,000 Daltons was obtained. This porosity was achieved by using 1.4% sodium alginate with an approximate molecular weight of 240,000 daltons entering a 0.2% citosan solution with an approximate molecular weight of 20,000 daltons. The length of polymerization time between sodium alginate and citosan is estimated to be seconds.

EXAMPLE 5

Fresh solution of polyanion, e.g. 1.4% sodium alginate and 0.8% $NaCl_2$ solution was prepared. The viscosity of the polyanion solution was determined to be 54 cp. Whole blood cells were admixed to the polyanion solution. The polyanion-cell solution was transferred to the first reservoir. A liquid jet flow from the first nozzle was observed. The barrel diameter of the first nozzle was 0.2 inch. The height of the first tank 14 was adjusted to obtain a hydrostatic pressure needed to have laminar flow of the polyanion jet, approximately three feet above the initial position. Then the hydrostatic pressure was adjusted to approximately the mid-range. The first oscillator was turned on. The first oscillator frequency and amplitude were adjusted so that the polyanion jet broke up into uniform size droplets. In this particular experiment the frequency of the oscillator was adjusted to between 1–4 kilohertz. The droplet size selected was between about 300 to 400 microns. The spheres were observed to determine if each sphere contained a cell. If the spheres do not contain cells the percent sodium alginate in reservoir one was reduced, to increase the concentration of cells in the solution. At this time the polyanion jet is turned off.

The polycation solution, $CaCl_2$ was transferred to reservoir two. The height of reservoir two was adjusted to produce a laminar annular flow from the nozzle. The hydrostatic pressure was set at one half of the maximum hydrostatic pressure to produce a laminar flow. The internal pressure between top and bottom chamber of the housing was then adjusted to slightly increase pressure within the top chamber. In the present apparatus about one psi of pressure is required to lengthen the annular jet without causing the stream to blow out. The pressure was set at two-thirds of the maximum pressure level in this apparatus. The second oscillator was turned on and the frequency was adjusted so that the annular polycation jet broke into uniform size droplets. In this example the oscillator was set at 0.5–2 kilohertz. The polyanion jet was then restarted. The three axis position and level adjuster was adjusted so that the polyanion and polycation jets met in the desired location on the horizontal plane. The external pressure was adjusted so that the polyanion droplet entered the annular jet at the desired vertical position. See FIG. 1. A capacitor deflector was used so that the number of polyanion droplets matched the number of polycation droplets per unit time. The capacitor in the apparatus has two plates with a pulsating voltage of approximately two kilovolts. The frequency was between the frequency selected for oscillators one and two. The rejected polyanion droplets could be reused.

Deformation of the microsphere was avoided by minimizing the impact velocities. The inventor found that both vertical and radial impact velocities must be reduced. In particular the droplet was submerged into the liquid sheet at approximately the same relative vertical velocity, i.e. they were falling at approximately the same rate. In this example the velocity of the droplet and annular jet was 1.5 m/sec. Second, the polyanion droplet was placed in the polycation stream to avoid turbulence. The turbulence normally associated with the collapsing of a jet was avoided by increasing the pressure inside of the annular jet to adjust the radial collapsing velocity of the jet. The radial collapsing velocity is the inward (horizontal) radial component of velocity which is perpendicular to the vertical velocity component.

The air flow pump was then turned on to adjust the rate so that the falling polycation droplets suffer minimum aerodynamic drag effects and remain spherical. The filter cloth belt and wash solution are used to collect encapsulated red blood cells.

ADDITIONAL MEMBRANE COMPOSITION

In addition to polymers, solutions capable of forming a solid mixture upon mixing can be used in this invention. These solutions include inorganic membranes and biological membranes.

BIOLOGICAL MEMBRANES

Biological membranes can exist in three forms: as monolayers, planar bilayers or as liposomes. All these are liquid structures. A liposome is simply any bilayer structure that encloses a volume, such as a micelle. The most common example of this type of membrane is a phospholipid, where multiple bilayers exist and form concentric shells much like an onion. These typically have diameters between 200 and 5000 A. the internal structure of each bilayer vescicle includes a polar, or hydrophilic, head attached to a long chain hydrocarbon tail(s). If the tails contain unsaturated groups then the bilayer can be post-polymerized with the addition of a free radical initiator such as AIBN (azobisisobutrylnitrile). Under such conditions we would no longer speak of a liquid membrane. Membrane lipids which are suitable for the formation of a bilayer are diverse and include the following classes of compounds:

- phospholipids
- lysophospholipids
- glycosyl diacylglycerols
- plasmalogens
- sphingomyelins
- gangliosides
- sterols The synthesis of these biological membranes involves the synthesis and isolation of the individual proteins or lipids and then the transportation of the lipids to their eventual interfacial site. The interaction of small molecules with biomembranes has also been extensively studied and a variety of diffusion and permeability data are available. Permeability is however effected by a classical Fickian like diffusion process with a concentration gradient acting as the driving force for transport across the membrane.

The formation of a stable liposome requires the temperature to exceed the gel-to-liquid crystal-transition temperature (Tc). This corresponds to the melting point of the acyl chains. All phospholipids have a Tc and this depends on the nature of the hydrophilic head and the degree of unsaturation on the hydrocarbon chain. The membrane formation is strongly influenced by the synthesis conditions, primarily heat, light and pH.

The interior of the lipid bilayers can be probed with a variety of a standard techniques including Raman and FTIR spectroscopy as well as proton NMR. Differential Scanning Calorimetry (DSC) is often used to obtain information on the thermodynamics of membrane formation.

The "multimellar" vesciles or lipid membranes are very heterodisperse with respect to size. The particle diameter is often lowered by exposing the vesicles to ultransonication. The size is generally measured through liquid chromatographic techniques.

The kinetics of the liposomes formation have not been studied. All researchers merely report a "spontaneous" formation when the amphipathic lipid is dispersed in an excess of water.

SYNTHETIC POLYMERIC MEMBRANES

Thin film polymeric membranes are advantageous for many biological applications since the permeation of solutes across the membrane in inversely related to the thickness. These thin film porous membranes are typically produced by either a "phase inversion" process or a complex coacervation reaction. Both processes can yield stable biocompatible microspheres and it remains to be resolved which process is superior. Phase inversion involves the synthesis of a membrane from an initially homogeneous polymer solution through the application of a temperature for composition change. Thermal inversion is more common and produced a fibrous like membrane structure. Sefton shows some electron micrographs of example capsules. He has also concluded that as the speed of precipitation increases the porosity also rises. M. V. Sefton, "Blood, Guts and Chemical Engineering," The Canadian J. of Chem. Eng. 67:705 (1989). This is similar to the effects that Wang reported for the membranes formed via complex coacervation. LLoyd (Materials Science of Synthetic Membranes) provides a comprehensive list of polymers used in the phase inversion technique. D. R. Lloyd, ed. "Materials Science of Synthetic Membranes," Amer. Chem. Soc. Washington, D.C. (1985).

Although the invention has been described primarily in connection with special and preferred embodiments, it will be understood that it is capable of modification without departing from the scope of the invention. The following claims are intended to cover all variations, uses, or adaptations of the invention, following, in general, the principles thereof and including such departures from the present disclosure as come within known or customary practice in the field to which the invention pertains, or as are obvious to persons skilled in the field.

I claim:

1. A method for producing uniform polymeric spheres from polyanion and polycation monomers comprising:
   a) providing droplets of a polyanion solution;
   b) providing a stream of polycation solution; and
   c) mixing said droplets of said polyanion solution and said stream of said polycation solution at substantially equal velocities along a common axis to minimize impact forces therebetween and under polymerization conditions to form uniform spheres.

2. The method of claim 1 wherein said stream of polycation solution forms an annular jet.

3. The method of claim 1 wherein said droplets of polyanion solution includes an encapsulant.

4. A method for producing uniform spheres from polyanion and polycation monomers comprising:
   a) providing droplets of a biocompatible polyanion monomer solution at a certain vertical velocity;
   b) providing a stream of polycation monomer solution wherein said stream of polycation forms an annular jet at approximately the same vertical velocity as the polyanion solution;
   c) adjusting the radial collapsing velocity of said annular jet to delay said jet from radially collapsing until said jet substantially envelopes said droplets and to minimize impact forces therebetween when said droplets and said stream are mixed; and
   d) mixing said droplets of polyanion solution and said polycation jet under polymerization conditions to form uniform spheres.

5. The method of claim 4 wherein the vertical velocity of the annular jet is adjusted by changing the hydrostatic pressure of the polycation solution.

6. The method of claim 4 wherein said radial collapsing velocity of the polycation jet is adjusted by increasing the pressure inside of said jet.

7. The method of claim 4 wherein said droplets of polyanion solution include an encapsulant.

8. A method for encapsulating biological material in a uniform polymeric sphere having porosity varying from semipermeable to impermeable from polyanion and polycation monomers comprising:
   a) selecting polycation and polyanion monomers to form a membrane of the desired porosity;
   b) admixing said polycation monomer solution and biological material;
   c) generating droplets consisting of said biocompatible polyanion monomer solution and said biological material falling at a certain vertical velocity;
   d) providing a stream of polycation monomer solution wherein said stream of polycation forms an annular jet at approximately the same vertical velocity as the polyanion solution;
   e) adjusting the radial collapsing velocity of said annular jet to delay said jet from radially collapsing until said jet substantially envelopes said droplets and to minimize impact forces therebetween when said droplets and said stream are mixed; and
   f) mixing said droplets and polycation jet under polymerization conditions for a set period of time to form uniform spheres of the desired porosity.

9. The method of claim 8 wherein the vertical velocity of the annular jet is adjusted by changing the hydrostatic pressure of the polycation solution.

10. The method of claim 8 wherein said radial collapsing velocity of the polycation jet is adjusted by increasing the pressure inside the annular jet.

11. The method of claim 8 wherein said biological material is living cells or tissues.

* * * * *

UNITED STATES PATENT AND TRADEMARK OFFICE
CERTIFICATE OF CORRECTION

PATENT NO. : 5,260,002

DATED : November 9, 1993

INVENTOR(S) : Taylor G. Wang

It is certified that error appears in the above-indentified patent and that said Letters Patent is hereby corrected as shown below:

Column 1, after line 7, insert -- This invention was supported by funding from NASA Grant No. NAGW 1707. --

Signed and Sealed this

Eleventh Day of October, 1994

Attest:

BRUCE LEHMAN

Attesting Officer          Commissioner of Patents and Trademarks